United States Patent [19]

Drake et al.

[11] 4,340,693

[45] Jul. 20, 1982

[54] TITANOBORATE GLASS AS CROSS-LINKING AGENT IN POLYCARBOXYLIC ACID CEMENTS

[75] Inventors: Cyril F. Drake; Francesca M. Shreeve, both of Harlow, England

[73] Assignee: International Standard Electric Corporation, New York, N.Y.

[21] Appl. No.: 197,863

[22] Filed: Oct. 17, 1980

Related U.S. Application Data

[63] Continuation of Ser. No. 91,905, Nov. 6, 1979, abandoned.

[30] Foreign Application Priority Data

Nov. 24, 1978 [GB] United Kingdom ............... 46019/78

[51] Int. Cl.$^3$ .......................... C03C 3/14; C08K 3/40
[52] U.S. Cl. ................................ 525/337; 128/87 R; 260/998.11; 524/5; 433/228; 501/49
[58] Field of Search ....................... 501/51, 46, 47, 49; 260/998.11, 42.52, 42.53, 29.6 M; 433/228; 128/87 R; 525/337

[56] References Cited

U.S. PATENT DOCUMENTS

| | | | |
|---|---|---|---|
| 3,814,717 | 6/1974 | Wilson et al. | 433/228 |
| 3,901,719 | 8/1975 | Brydges et al. | 501/49 |
| 3,962,267 | 6/1976 | Suzuki et al. | 433/228 X |
| 4,123,416 | 10/1978 | Potter et al. | 433/228 X |
| 4,174,334 | 11/1979 | Bertenshaw et al. | 260/29.6 M |
| 4,188,317 | 2/1980 | Temin | 260/42.53 |
| 4,250,277 | 2/1981 | Maries et al. | 525/337 |
| 4,271,057 | 6/1981 | Drake et al. | 260/29.6 M |

FOREIGN PATENT DOCUMENTS 2035290  6/1980  United Kingdom ............... 525/337

*Primary Examiner*—Helen M. McCarthy
*Attorney, Agent, or Firm*—John T. O'Halloran; Robert P. Seitter

[57] ABSTRACT

A range of titano-borate glass compositions e.g. for use as cross linking agents in the preparation of polycarboxylic acid cements. The glass may contain one or more further metal oxides, for example calcium and/or zinc, and typically comprises 25-40 mole % calcium, 45-65 mole % boric oxide and up to 15 mole % titanium dioxide. The specification also describes the preparation of polycarboxylic acid, typically polyacrylic acid, cements incorporating the glasses.

9 Claims, No Drawings

TITANOBORATE GLASS AS CROSS-LINKING AGENT IN POLYCARBOXYLIC ACID CEMENTS

This is a continuation of application Ser. No. 091,905, filed Nov. 6, 1979, abandoned.

This invention relates to glass compositions such as are employed in the preparation of polycarboxylic acid water setting cements and to cement compositions incorporating such glasses.

It is well-known that polycarboxylic acids such as described in our co-pending Application No. 50,578/76 can be crosslinked to form a solid cement by treatment in an aqueous medium with a controlled supply of divalent or polyvalent metal ions.

Two stages are observed in the process of setting of such cements. During the first stage the viscosity of the aqueous mix increases rapidly, but it may still be stirred, poured, cast or otherwise worked to give a desired shape to the finished product. This state terminates after a period $t_w$ known as the working time, when the mixture has achieved sufficient rigidity to prevent further working. During the second stage the material develops considerably greater mechanical strength until the setting time $t_s$, which is arbitrarily defined as the time which the cement achieves a rigidity or strength appropriate to a particular use.

In many applications such as those where the set cement perform a structual or reinforcing role, it is desirable to provide a curable cement having a relatively long $t_w$ so that it may be mixed to a sufficiently homogeneous paste to ensure the subsequent development of high strength in the set cement. Previously ion leachable glasses or alumino-borate glasses have been used for this purpose.

According to one aspect of the invention there is provided a partially or completely water soluble glass composition as hereinafter defined adapted to provide cross linking of a polycarboxylic acid cement, said composition including a titano-borate glass containing at least one further metal oxide.

According to another aspect of the invention there is provided a cement composition comprising a polycarboxylic acid material, and a partially or completely water soluble glass as hereinafter defined, said glass comprising a titanoborate glass containing at least one further metal oxide.

The term 'glass' as employed herein is understood to include not only homogeneous glass systems, but also partially devitrified and phase separated materials.

The term 'poly carboxylic acid' as used herein is understood to include polymers of unsaturated monocarboxylic acids and their anhydrides, unsaturated dicarboxylic acids and their anhydrides or copolymers formed from combinations thereof. Copolymers may also be formed from such materials together with other ethylenically unsaturated monomers. Specific monomers are acrylic, litaconic, mesaconic, citraconic or maleic acids or their respective anhydrides. The polycarboxylic acid may be in dry powder form or in aqueous solution.

The glass compositions are prepared by fusing the constituent oxides, or compounds which on heating decompose to form the respective oxides, for a sufficient period of time to form an homogeneous melt. Typically, quantities of titanium dioxide and boric oxide, which latter acts as the glass forming oxide of the system, are fused together with one or more further metal oxides at a temperature of 1,000° to 1,500° C. in an oxidizing atmosphere. The one or more further metal oxides may act as cross-linking agents for polycarboxylic acid materials and for this purpose should comprise divalent or polyvalent metal oxides. To produce a desired glass composition it may be necessary to add an excess of boric oxide to the initial mix as some of this oxide is lost by evaporation during the fusion process.

The molten glass is quenched to form a solid material which is then crushed and ground to a fine powder, the degree of fineness depending on the particular application of the glass material. The exact composition of the glass may then be determined by chemical analysis of the powder.

The water solubility rate of the glass composition may be adjusted by incorporation of suitable further metal oxides. Thus, for example, calcium oxide reduces the solubility of the glass and also acts as a cross-linking agent for polycarboxylic acid materials. Other metals which may be incorporated by way of their oxides include zinc, magnesium, barium, strontium, copper, iron nickel, cobalt or mixtures thereof. The glass may also incorporate one or more alkali metal oxides for the purpose of increasing water solubility. Preferred glass compositions comprise 25-40 mole % calcium oxide, 45 to 65 mole % boric oxide and up to 15 mole % titanium dioxide. Optionally such compositions may also include up to 15 mole % zinc oxide. This limit should not be exceeded where X-ray transparency of the cement is required. However, in other applications the zinc content may of course be increased above this level.

The glass compositions may be employed in the preparation of polycarboxylic acid cements. Typically, weighed quantities of the powdered glass and the polycarboxylic acid, either in dry powder of aqueous solution form, are mixed together. Where the dry powders are employed sufficient water is added to initiate the cross-linking reaction. Setting of the cement generally proceeds in two stages during the first of which the material may be worked or moulded to the desired shape.

The preferred polymer materials for use with the glasses described herein are those based on acrylic acid. Thus, preferred homopolymers are acrylic acid or acrylic anhydride homopolymers. Acrylic acid copolymers preferably incorporate acrylamide or acrylonitrile as the ethylenically unsaturated monomer. Acrylic anhydride copolymers preferably incorporate ethylene, propylene, butane or styrene as the ethylenically unsaturated monomer. The number average molecular weight of the polymeric material may be from 1,000 to 1,000,000, materials within the range 1,000 to 500,000 being preferred.

In some applications, for example dental applications it is advantageous to provide a dry pack mix of the glass and polycarboxylic acid, the cement being formed when required by adding a suitable quantity of water immediately prior to use. Thus, sufficient water may be added to form a thick paste which is injected into a tooth cavity and allowed to set. It is thought that the calcium ions present in the tooth interact with the polycarboxylic acid material and thus firmly bond the cement to the tooth.

In order to extend the setting times of cements formed with the glass compositions described herein, the glass may be subjected to one of the phosphate, treatments described in our co-pending application No. 091,915 (C. F. Drake-N. R. Adams 66-1), U.S. Pat. No.

4,271,057. In such a treatment glass particles are either coated with or used in conjunction with a phosphate material such as phosphoric acid, phosphorus pentoxide or an inorganic phosphate. The reaction mechanism is not fully understood, but the effect of such treatment is to extend the working time of the cement incorporating the glass without significantly extending the setting time of the cement. This of course greatly extends the range of glass compositions which may be employed and the range of applications for which cements incorporating such glasses may be used.

Typical therapeutic uses of cements formed from the glass compositions described herein include dental cements, orthopaedic cements, e.g. for splint bandages, and cements for the construction of prostheses such as are employed as human joint replacements. Other applications include but are not limited to structual cements which, advantageously, may be reinforced e.g. with glass plastics or carbon fibres, quick setting cements e.g. for emergency repairs to roads or aircraft runways, soil stabilization cements, vehicle body filler materials and grouting cements. In some applications the cements may contain additives. Thus a tile grouting cement may include a fungicide and/or a bacteriocide to prevent the growth of micro-organism. Similarly, a vehicle body cement may include a metal corrosion inhibitor.

The following Example illustrates the invention.

EXAMPLE

A range of glass compositions was prepared by co-melting calcium oxide, boric oxide and titanium dioxide, in some cases together with zinc oxide. The glasses were fused in an oxidizing atmosphere for 2 hours at a temperature of 1100°–1200° C. and were then quenched by casting on to a cooled steel plate and were crushed, ground and sieved to an average particle size of 45 microns. The composition of each glass was determined by chemical analysis.

Weighed quantities of each glass were mixed with powdered polyacrylic acid (PAA) and water was added to initiate the setting reaction. In all cases the weight ratio of glass to PAA to water was 3:1:2. The setting characteristics were determined in each case, the results being summerised in the following table

TABLE 1

| Batch No. | Glass composition - Mole % | | | | Working Time | Setting Time |
|---|---|---|---|---|---|---|
| | CaO | $B_2O_3$ | ZnO | $TiO_2$ | | |
| CTB2/2 | 30 | 65 | — | 5 | 25 sec | 3 min |
| CTB2/3 | 35 | 60 | — | 5 | 30 sec | 4 min |
| CTB2/9 | 35 | 55 | — | 10 | 35 sec | 100 min |
| CTB2/10 | 40 | 55 | — | 5 | 20 sec | 15 min |
| CTB2/1 | 35 | 46.5 | 12.5 | 6 | 20 sec | 5 min |

In addition, samples of the glasses were phosphated to a level of 2 mole % phosphorus by treatment with an aqueous ammonium dihydrogen phosphate solution followed by drying and crumbling of the cake thus obtained. As before weighed samples of the glasses were mixed with PAA and water in a weight ratio 3:1:2 and the setting characteristics were determined. The results are summarized in the following table:

TABLE 2

| Batch No. | Composition Mole % | | | | Working Time | Setting Time |
|---|---|---|---|---|---|---|
| | CaO | $B_2O_3$ | ZnO | $TiO_2$ | | |
| CTB2/2 | 30 | 65 | — | 5 | 80 sec | 10 min |
| CTB2/3 | 35 | 60 | — | 5 | 90 sec | 10 min |
| CTB2/9 | 35 | 55 | — | 10 | 130 sec | 70 min |
| CTB2/10 | 40 | 55 | — | 5 | 65 sec | 5 min |
| CTB2/1 | 35 | 46.5 | 12.5 | 6 | 40 sec | 2 min |
| CFD/1 | 35 | 50 | 12.5 | 2.5 | 50 sec | 4.5 min |
| CFD/2 | 33 | 50 | 12 | 5 | 46 sec | 7 min |
| CFD/3 | 31 | 50 | 11.5 | 7.5 | 95 sec | 8.5 min |
| CFD/4 | 30 | 50 | 10 | 10 | 240 sec | 40 min |
| CFD/5 | 28 | 50 | 9.5 | 12.5 | 780 sec | 40 min |

In all cases it was found that the shrinkage of the cement on setting was very low, generally less than 1%, and for titanium dioxide concentrations equal to those of alumina in equivalent aluminoborate glasses then shrinkage was found in every case to be lower than that experienced with cements formed from aluminoborate glasses.

We claim:

1. A water setting cement composition comprising a polycarboxylic acid material, and a partially or completely water soluble glass composition, said glass composition acting as a cross-linking agent and comprising a titanoborate glass containing CaO as at least one further metal oxide said titanoborate glass having no alumina whereby shrinkage upon setting is generally less than 1% and is lower than that experienced with cements formed from aluminoborate glasses.

2. A cement composition as claimed in claim 1, and wherein the polycarboxylic acid is a polyacrylic acid homopolymer or copolymer.

3. A cement composition as claimed in claim 2, and wherein said polyacrylic acid has a number average molecular weight of $10^3$ to $10^6$.

4. A cement composition as claimed in any one of claims 1, 2, or 3, and wherein said glass composition incorporates phosphous pentoxide.

5. A cement composition as claimed in any one of claims 1, 2, or 3 and wherein said cement composition incorporates a phosphate material.

6. A cement composition as claimed in any one of claims 2, or 3 and in which said cement composition is reinforced with glass, plastic or carbon fibres.

7. A splint bandage incorporating a cement composition as claimed in any one of claims 2, or 3.

8. A dry pack mix for the preparation of a water setting cement composition, said mix comprising a polycarboxylic acid in powder form together with a titanoborate glass containing CaO as at least one additional metal oxide said titanoborate glass having no alumina whereby shrinkage upon setting is generally less than 1% and is lower than that experienced with cements formed from aluminoborate glasses.

9. A cement composition as claimed in any one of claims 1, 2, or 3 and which incorporates a fungicide, a bacteriocide, a metal corrosion inhibitor or mixtures thereof.

* * * * *